(12) United States Patent
Cancel et al.

(10) Patent No.: US 7,457,668 B2
(45) Date of Patent: Nov. 25, 2008

(54) METHOD AND DEVICE FOR REMOTE AND NONCONNECTED IMPLEMENTATION OF AN IMPLANT AND IMPLANT IMPLEMENTED BY SAID DEVICE

(75) Inventors: Richard Cancel, La Garde (FR); Richard Wallace, Gonfaron (FR); Gerard Sassi, Roulon (FR)

(73) Assignee: Europlak (FR)

( * ) Notice: Subject to any disclaimer, the term of this patent is extended or adjusted under 35 U.S.C. 154(b) by 133 days.

(21) Appl. No.: 10/444,162

(22) Filed: May 23, 2003

(65) Prior Publication Data

US 2003/0225440 A1 Dec. 4, 2003

Related U.S. Application Data

(63) Continuation of application No. PCT/FR01/03704, filed on Nov. 23, 2001.

(30) Foreign Application Priority Data

Nov. 23, 2000 (FR) ................................. 00 15140

(51) Int. Cl.
*A61N 1/00* (2006.01)
(52) U.S. Cl. ........................ 607/59; 604/909
(58) Field of Classification Search ............ 607/30–32, 607/59–60; 606/157; 600/29–31; 604/909
See application file for complete search history.

(56) References Cited

U.S. PATENT DOCUMENTS

| 4,681,111 | A | * | 7/1987 | Silvian | 607/59 |
| 5,058,581 | A | * | 10/1991 | Silvian | 607/32 |
| 5,354,319 | A | | 10/1994 | Wyborny et al. | |
| 5,879,375 | A | * | 3/1999 | Larson et al. | 607/30 |
| 5,938,669 | A | * | 8/1999 | Klaiber et al. | 606/157 |
| 6,106,551 | A | * | 8/2000 | Crossett et al. | 623/3.28 |
| 6,115,636 | A | * | 9/2000 | Ryan | 607/60 |
| 6,210,347 | B1 | * | 4/2001 | Forsell | 600/593 |
| 6,547,801 | B1 | * | 4/2003 | Dargent et al. | 606/157 |

FOREIGN PATENT DOCUMENTS

| EP | 0 619 101 A1 | 10/1994 |
| WO | WO 96/22049 | 7/1996 |
| WO | WO 98/43700 | 10/1998 |
| WO | WO 00/15158 | 3/2000 |
| WO | WO 00/30534 | 6/2000 |

\* cited by examiner

*Primary Examiner*—George R Evanisko
(74) *Attorney, Agent, or Firm*—DLA Piper (US) LLP

(57) ABSTRACT

A method for remote and nonconnected interaction between an implant having an electrical motor and a transmitter/receiver inverter having an induction source having/connected to a power source for operating the electrical motor including creating modifications in an electromagnetic field by the transmitter/receiver inverter, and transmitting information in the form of binary data from the transmitter/receiver inverter to the implant; and a device for remote and nonconnected interaction with an implant having a transponder including an induction source having/connected to a power source, and means enabling the induction source to create modifications in an electromagnetic field generated in the device to transmit information in the form of binary data to the implant.

6 Claims, 2 Drawing Sheets

METHOD AND DEVICE FOR REMOTE AND NONCONNECTED IMPLEMENTATION OF AN IMPLANT AND IMPLANT IMPLEMENTED BY SAID DEVICE

RELATED APPLICATION

This is a continuation of International Application No. PCT/FR01/03704, with an international filing date of Nov. 23, 2001, which is based on French Patent Application No. 00/15140, filed Nov. 23, 2000.

FIELD OF THE INVENTION

This invention relates to the field of remote and nonconnected implementation of an implant comprising electrical instrumentation. More particularly, the invention relates to a method and device for remote and nonconnected implementation of an implant comprising electrical instrumentation, the implementation device comprising an induction source constituting a power source for the operation of the electrical instrumentation.

BACKGROUND

Already known in the prior art are methods and devices for the remote and nonconnected implementation of implants comprising electrical instrumentation. WO 00/15158 is one example. It discloses a gastric constriction device of a particular type which can be implemented remotely and in a nonconnected manner by means of a transmitter comprising an induction source. The induction source transmits the power required for the implementation of the motor and particular frequencies are selected: one to trigger a forward movement command and the other to trigger a rearward movement command.

A major disadvantage of this device is the fact that the only transmittable commands are forward movement/rearward movement. There is no means to verify via the device that the command was received, that it was executed and to what extent it was executed. Moreover, this device does not provide all necessary guarantees against an untimely implementation of the implant's electrical instrumentation.

There are also implementation devices capable of communicating with the implants. However, in these systems, the implant has its own power source for operating the electrical instrumentation (motor or other). This is not practical for implants requiring large amounts of power in terms of power consumption or duration because it then becomes necessary to regularly change the power source during a surgical operation.

It would, therefore, be advantageous to resolve the disadvantages of the prior art by providing an implementation method and device according to which the implementation device is capable of both communicating with the implant by sending information in the form of binary data and also providing a power source for the implant for operating the electrical instrumentation that it carries by means of a single means, an induction source. It would also be advantageous to provide an implant capable of both communicating with the implementation device by sending it information in the form of binary data and also receiving the power required for the operation of the electrical instrumentation that it carries.

SUMMARY OF THE INVENTION

The invention relates to a method for remote and nonconnected interaction between an implant having an electrical motor and a transmitter/receiver inverter having an induction source having/connected to a power source for operating the electrical motor including creating modifications in an electromagnetic field by the transmitter/receiver inverter, and transmitting information in the form of binary data from the transmitter/receiver inverter to the implant.

The invention also relates to a device for remote and nonconnected interaction with an implant having a transponder including an induction source having/connected to a power source, and means enabling the induction source to create modifications in an electromagnetic field generated in the device to transmit information in the form of binary data to the implant.

The invention further relates to a gastric constriction implant capable of being installed remotely in a patient including the device for remote and nonconnected interaction with an implant.

BRIEF DESCRIPTION OF THE DRAWINGS

Better comprehension of the invention will be obtained from the description below, presented in a purely explanatory manner, of one mode of implementation of the invention with reference to the attached figures.

DETAILED DESCRIPTION

Figure 1:
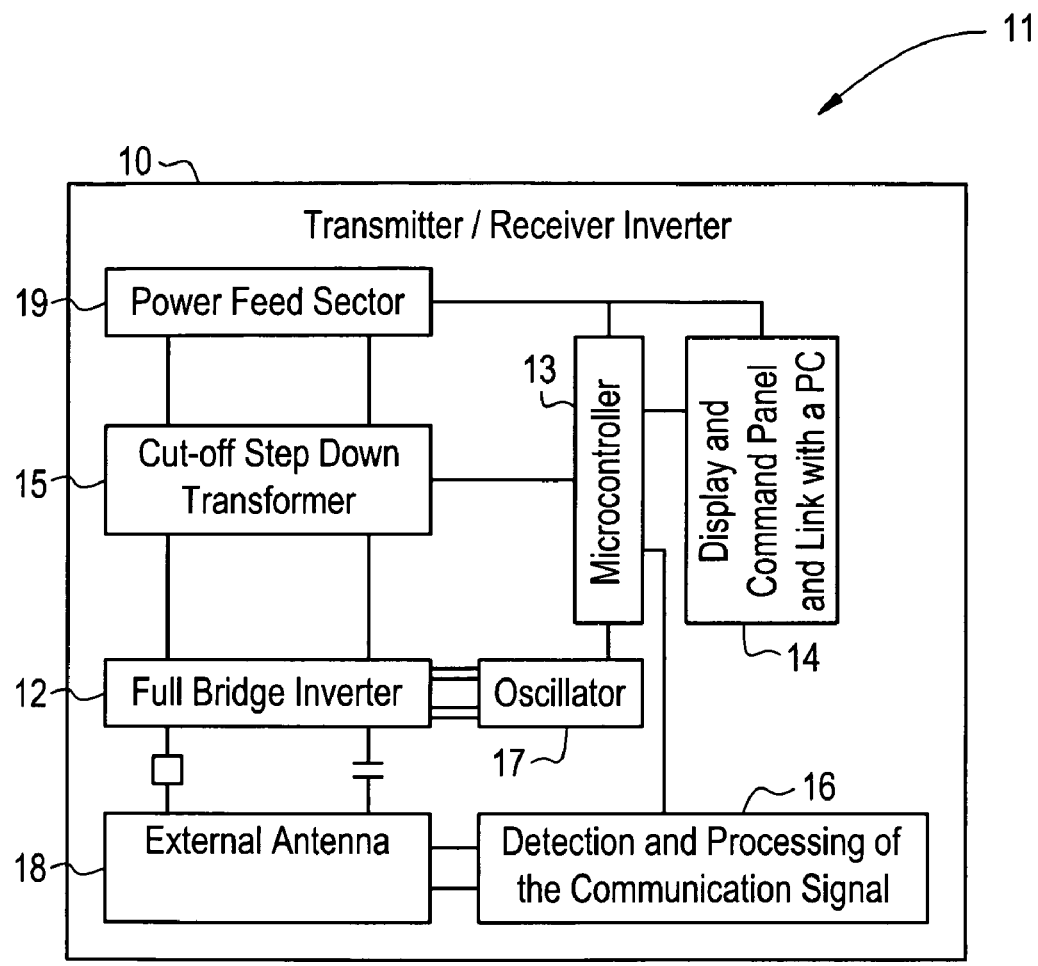
FIG. 1 is a schematic diagram of the device for remote and nonconnected implementation of an implant and the implant implemented by this device according to the invention.
Figure 1:
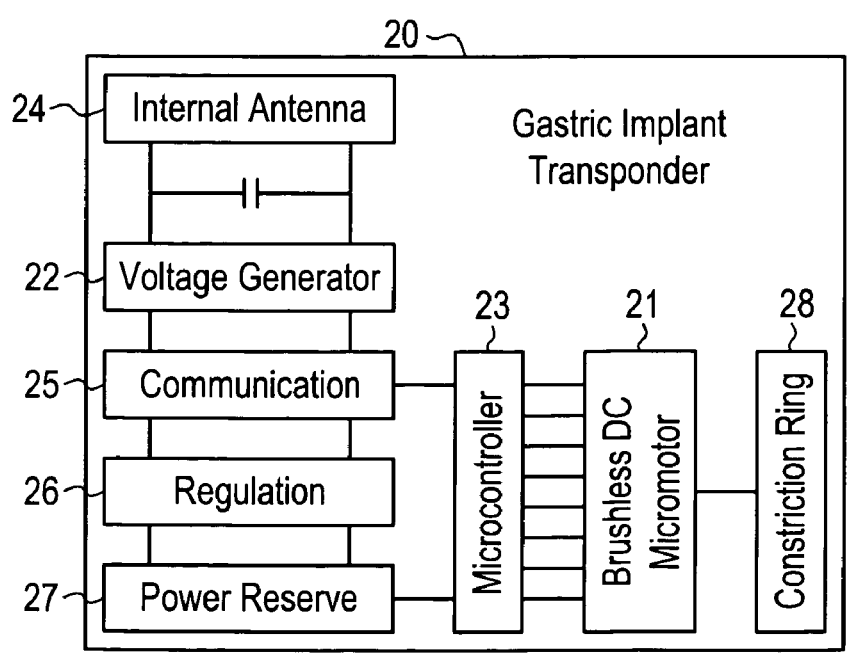

According to the invention, modifications are made in the implementation of the electromagnetic field by the induction source to transmit information in the form of binary data to an implant. Information transmission is performed advantageously by means of bits which are optionally delayed. Information transmission is performed advantageously from the implementation device to the implant and vice versa.

The information advantageously pertains alternatively or cumulatively to:
 the serial number of the implant;
 the identification of the patient;
 the date of initial operation;
 the date of the last intervention;
 the number of interventions;
 the state of the implant;
 the history of the content of the interventions;
 the acknowledgments of receipt of the transmissions; and
 the confirmation of the implementation of the action.

The acknowledgments of receipt of the transmissions are advantageously constituted by particular bits.

The invention, thus, pertains to a device for the remote and nonconnected implementation of an implant comprising electrical instrumentation, the implementation device comprising an induction source constituting a power source for the operation of the electrical instrumentation, the implementation device furthermore comprising means enabling the induction source to implement modifications in the electromagnetic field to transmit information in the form of binary data to said implant.

The means enabling the implementation of modifications in the creation of the electromagnetic field are advantageously constituted of an inverter coupled with a transmitter antenna. The antenna is also preferably coupled to a receiver and the implementation device comprises a module for the detection and processing of the modifications that have occurred in the electromagnetic field.

The device advantageously comprises a microcontroller connected to a display and command device and/or capable of communicating with a computer functioning as interface. The implementation device advantageously also comprises a cut-off step-down transformer to enable optimization of the amplitude of the electromagnetic field. The invention also pertains to an implant, especially a gastric constriction device, capable of being installed remotely and in a nonconnected manner by an implementation device according to the invention. The implant advantageously comprises means to enable creation of modifications in the electromagnetic field to transmit information in the form of binary data to the implementation device.

The means to enable creation of modifications in the electromagnetic field are advantageously constituted of a communication module.

The information transmitted by the implant advantageously pertains alternatively or cumulatively to:
  the serial number of the implant;
  the identification of the patient;
  the date of initial operation;
  the date of the last intervention;
  the number of interventions;
  the history of the content of the interventions;
  the acknowledgments of receipt of the transmissions; and
  the confirmation of the implementation of the action.

The acknowledgments of receipt of transmissions are, moreover, preferably constituted of particular bits. The implant advantageously comprises a microcontroller connected to the means enabling creation of modifications in the electromagnetic field. The electrical instrumentation is advantageously a brushless motor with rotor position sensor(s).

The method for remote and nonconnected implementation of the invention is a method for implementation of an implant (20) comprising electrical instrumentation (21) by means of an implementation device (10), the implementation device comprising an induction source (11) constituting a power source for the operation of the electrical instrumentation (21).

The method according to the invention is characterized in that modifications are created in the implementation of the electromagnetic field by the induction source (11) to transmit information in the form of binary data to the implant (20). The implementation of this procedure is implemented after the implant has been implanted in the body. It is, therefore, implemented by trained personnel, but apart from any surgical intervention.

The transmission of information is operated by means of bits, optionally delayed, the bits being capable of forming words such as, for example, octets.

The implementation device (10), thus, comprises means for creating modifications in the implementation of the electromagnetic field by the induction source (11) to transmit information in the form of binary data to the implant (20).

The implementation device (10) according to the invention was developed for the control of an implant (20) creating a gastric constriction ring but it can also be adapted to any type of implant using electrical instrumentation.

The aspect of the invention illustrated in FIG. 1 is based on two elements: a transmitter/receiver inverter (11) on the one hand and an implant (20) transponder on the other hand.

Transmitter/receiver inverter: this is the system that provides power to the gastric implant, manages communications and creates the human/machine interface. It can be materially constituted by one or more parts. This system comprises the following elements:

The sector feed (19): it guarantees the insulation of the sector, integrates a power factor corrector (PFC), provides the power necessary for the operation of the step-down (15) and the inverter (12) as well as the command voltages.

Cut-off voltage step-down (15): it enables modulation of the intensity of the electromagnetic field on demand.

Full bridge inverter (12): this structure is needed to control the voltage applied to the resonant circuit. It provides voltage of square form. The modulation of the amplitude is solely managed by the step-down (15). This makes it possible to limit the frequency of commutation of the electronic switches.

External antenna (18): this is the coil that generates the electromagnetic field required for the operation of the implant. It also receives the signals originating from the implant (20). It is associated with a condenser and a resistor to constitute the resonant circuit.

Module (16) for detection and processing of the communication signal: this module enables extraction of data from the slight variation in voltage at the terminals of the external antenna and/or the current shifting.

Oscillator (17): it generates the command signals of the full bridge inverter (12). These signals are set by a very precise clock.

Microcontroller (13): it controls all of the systems. It manages in particular the communications, the amplitude of the electromagnetic field and the human/machine interface.

Display and command device (14) and/or link to a personal computer: on the display are found all of the data communicated by the implant. Information such as, for example, the name of the patient are input by means of an integrated keyboard of the type used for personal computers. A serial connector enables communication with a personal computer, for example, for maintenance of the device.

Implant (20) transponder:

Internal antenna (24): it is by means of this coil that the implant is powered and communicates with the exterior. It is associated with a condenser to create a resonant circuit calibrated at the same frequency as that of the inverter.

Voltage generator (22): generates a voltage from the power received by the antenna (24).

Communication module (25): communication is based on the transponder principle. Modification of the voltage at the terminals of the internal antenna causes a slight change in the amplitude of the voltage at the terminals of the external antenna and also a modification of the shifting of the current in the external resonant circuit. The inverter cuts the induction during a brief instant to transmit the date. This break is detected by the microcontroller (23) of the implant (20).

Regulation module (26): it limits the voltage at the terminals of the microcontroller (23).

Power reserve (27): it allows the microcontroller (23) to be powered during certain communication phases.

Microcontroller (23): this is the only complex circuit of the implant. It manages all communications and it also directly controls the electrical instrumentation (21) while controlling the amplitude of the constriction.

Electrical instrumentation (21): for example, a micromotor of the DC brushless type provided with rotor position sensor(s). This type of motor, which is almost wear-free, makes it possible by construction to know precisely the rotation number that it performs.

Constriction ring (28): it is actuated by the micromotor by a screw-bolt system.

The implant (20) is powered by induction. The induction is at a fixed frequency, e.g., 115.2 kHz. The waveforms are sinusoid.

The implant (20) comprises a microcontroller (23) which on the one hand controls the electrical instrumentation (21) constituted of the micromotor and on the other hand enables communication with the implementation device (10) and the storage of data.

The implant (20) communicates with the exterior by modifying the voltage at the terminals of its antenna (24). This modification is manifested by a modification of the voltage applied to the external antenna (18) and the shifting of the current. The duration of these modifications is processed then the signal is interpreted by the microcontroller (13) of the inverter.

Breaks are implemented in the electromagnetic field to communicate from the exterior to the implant (20). The implant is then powered by its energy reserve (27) and measures the duration of the breaks to extract the data from them.

From the interior to the exterior, the durations of the modifications are, for example, 500 µs for a logical 0, 1 ms for a logical 1 and 2 ms for the acknowledgment of receipt. One bit is transmitted every 2 ms.

From the exterior to the interior, the durations of the modifications are, for example, 750 µs for a logical 0, 1.5 ms for a logical 1 and 3 ms for the acknowledgment of receipt. One bit is transmitted every 3 ms.

The format of the data transmitted by the implant (20) is, for example:

Serial number of the implant coded over 4 octets
Patient identifier coded over 30 octets
Date of first use over 6 octets
Date of last intervention over 6 octets
History of the positions over 4 octets or 8 positions (position of the ring coded on 3 bits two positions per octet)
Number of interventions over 1 octet The format of the data transmitted to the implant (20) is the following:

In programming mode
Confidential code coded over 1 octet
Implant identifier coded over 4 octets
Patient identifier coded over 30 octets
Date of first use over 6 octets
In normal mode
Implant identifier coded over 4 octets
New position to be attained coded over 1 octet
Solely after displacement confirmed, date over 6 octets It is possible to transmit a "passe-partout" serial number that can control the ring to make the procedure secure, particularly in the case of poor communication of the implant.

In both directions of communication, each octet of data transmitted is directly preceded by its address over 1 octet and directly followed by 4 bits corresponding to the check sum of the transmitted word. The receiver transmits the acknowledgment of receipt. If there is no error, the transmitter than transmits the next data. If the transmitter does not receive the acknowledgment of receipt, it reattempts to transmit the same data and can make up to ten attempts. This totally original type of communication protects against any misinterpretation or "pirating" originating from another induction system of the same frequency.

The amplitude of the electromagnetic field is permanently modulated in relation to the requirements of the implant so as to limit the power to that which is strictly necessary. The internal antenna (24) is located in the implant (20). The antenna is positioned in a manner such that its axis is as perpendicular to the skin as possible.

For a clear understanding of the invention, it is important to understand that the term "nonconnected" means a lack of physical connector such as, e.g., a cable. There is, therefore, no need for an electric connection by cable between the implant (20) and the implementation device (10).

The external antenna (18) is applied to the skin of the patient to operate the implant. Upon application of voltage, the amplitude of the field is optimized to obtain communication with the implant. The implant transmits all of the data after various control operations. Once these data have been received correctly, they are displayed on the display and command device (14) of the implementation device (10). The operator can then select the new position to be attained. These data are transmitted to the implant (20) after confirmation. The field then increases to transmit the required power to the micromotor. Information is transmitted to the implementation device (10) and the field returns to its nominal value at the end of the displacement. The implementation device (10) interrogates the implant as to whether the displacement was correctly implemented and informs the operator.

Figure 2:
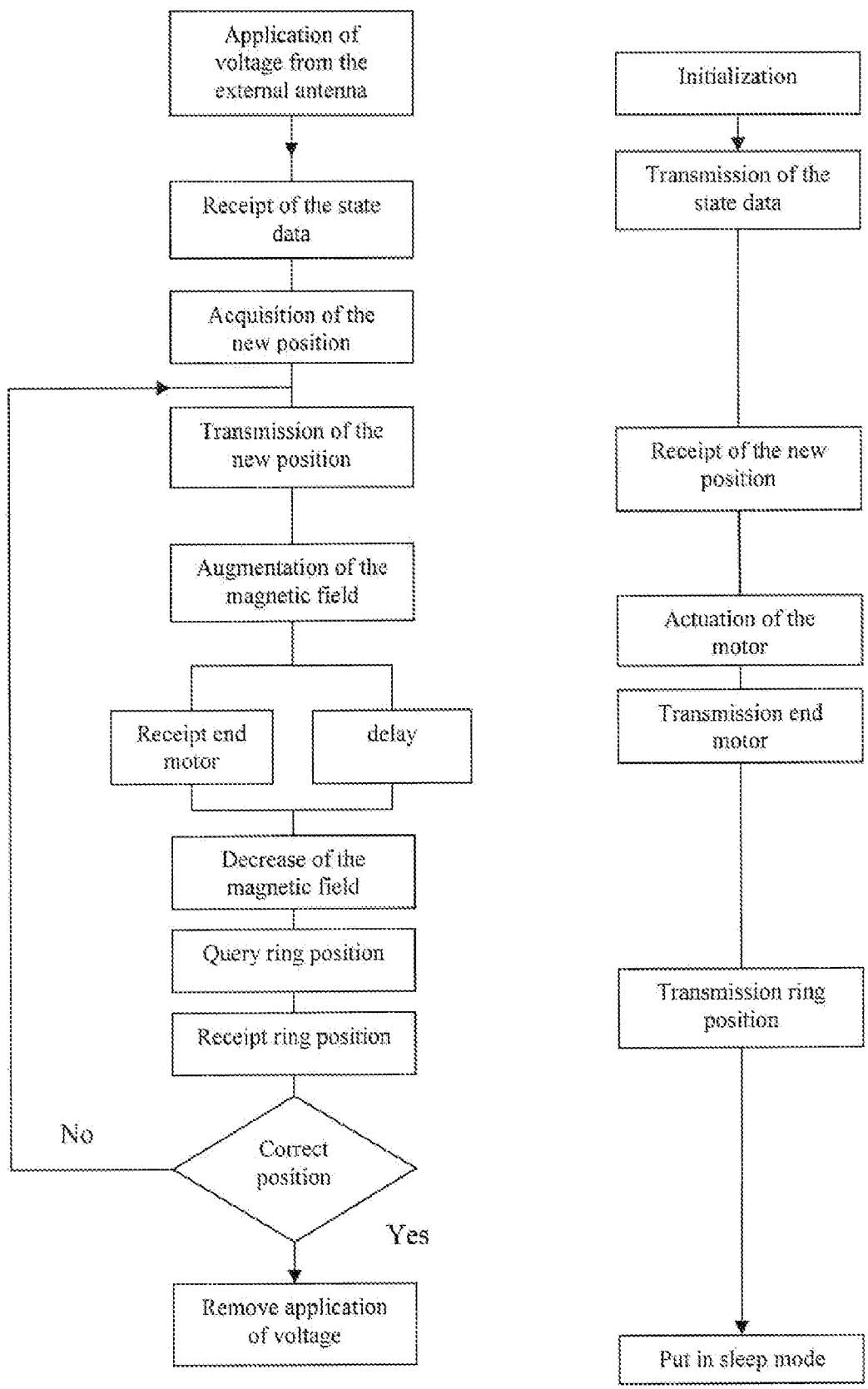
FIG. 2 is a simplified flowchart of the operation of the implementation device/implant assembly.

FIG. 2 illustrates a synoptic of the system. Thus. FIG. 2 shows a method for controlling a gastric constriction ring with a control device lacking a physical connector between the control device and the ring, wherein the gastric constriction ring comprises an electrical motor and the control device comprises an induction source having a power source for operating the electrical motor, comprising:

a) transmitting displacement instructions for positioning the gastric constriction ring in the form of binary data to the gastric constriction ring by selectively interrupting an electromagnetic field generated by the induction source;

b) receiving end motor instructions from the gastric constriction ring;

c) querying the ring position to the gastric constriction ring;

d) receiving the ring position;

e) checking whether the ring position is correct; and f) returning to a) if the ring position is not correct and turning off the control device if the ring position is correct.

The invention was described above as an example. It is understood that an expert in the field could implement different variations of the invention without going beyond the scope of the patent.

The invention claimed is:

1. A method for controlling a gastric constriction ring with a control device lacking a physical connector between the control device and the ring, wherein the gastric constriction ring comprises an electrical motor and the control device comprises an induction source having a power source for operating the electrical motor, comprising:

a) transmitting displacement instructions for positioning the gastric constriction ring in the form of binary data to the gastric constriction ring by selectively interrupting an electromagnetic field generated by the induction source;

b) receiving end motor instructions from the gastric constriction ring;

c) querying the ring position to the gastric constriction ring;

d) receiving the ring position;

e) checking whether the ring position is correct; and f) returning to a) if the ring position is not correct and turning off the control device if the ring position is correct.

2. The method according to claim 1, wherein transmission of the position of the gastric constriction ring is in bits which are optionally delayed.

3. The method according to claim 1, further comprising transmitting information from the gastric constriction ring to a transmitter/receiver inverter.

4. The method according to claim 1, wherein the binary data includes alternatively or cumulatively of:
a serial number of the gastric constriction ring;
identification of a patient;
a date of initial operation;
a date of last intervention;
a number of interventions;
a state of the gastric constriction ring;
a history of content of interventions;
acknowledgments of receipt of transmissions; and
a confirmation of implementation of an action.

5. The method according to claim 4, wherein acknowledgments of receipt of transmissions are constituted of particular bits.

6. The method according to claim 1 further comprising increasing the magnetic field to transmit power to the electric motor after the displacement instructions transmission (a); and decreasing the magnetic field after receiving end motor instructions from the gastric constriction ring (b).

* * * * *